(12) United States Patent
Liu et al.

(10) Patent No.: US 6,875,403 B2
(45) Date of Patent: Apr. 5, 2005

(54) METHOD AND APPARATUS FOR REPRODUCIBLE SAMPLE INJECTION ON MICROFABRICATED DEVICES

(75) Inventors: Shaorong Liu, Tracy, CA (US); Juan Lu, Tracy, CA (US)

(73) Assignee: Microchem Solutions, Lubbock, TX (US)

( * ) Notice: Subject to any disclaimer, the term of this patent is extended or adjusted under 35 U.S.C. 154(b) by 104 days.

(21) Appl. No.: 10/076,012

(22) Filed: Feb. 11, 2002

(65) Prior Publication Data

US 2002/0155032 A1 Oct. 24, 2002

Related U.S. Application Data

(60) Provisional application No. 60/267,474, filed on Feb. 9, 2001.

(51) Int. Cl.[7] .............................. B01L 3/02; B01L 11/00; G01N 15/06; G01N 33/00; G01N 33/48

(52) U.S. Cl. ........................ 422/100; 422/50; 422/55; 422/58; 422/63; 422/68.1; 422/81; 422/82; 422/101; 422/102; 422/103; 422/104; 436/43; 436/63; 436/164; 436/174; 436/180; 436/177; 436/178; 73/1.01; 73/1.02; 73/53.01; 204/403.01; 204/403.02; 204/403.03; 204/193; 435/283.1; 435/286.5; 435/286.6; 435/287.1; 435/287.2; 435/287.3; 435/288.4; 435/288.5; 435/288.7

(58) Field of Search ................... 422/50, 55, 58, 422/63, 68.1, 81, 82, 100, 101, 102, 103, 104, 939, 940, 942, 946, 948, 947; 436/43, 63, 164, 174, 180, 177, 178; 73/1.01, 1.02, 53.01; 204/403.02, 403.03, 193; 435/283.1, 286.5, 286.6, 287.1, 287.2, 287.3, 288.4, 288.5, 288.7

(56) References Cited

U.S. PATENT DOCUMENTS

| | | | | |
|---|---|---|---|---|
| 3,885,439 A | * | 5/1975 | Stone | 73/863.73 |
| 4,506,558 A | * | 3/1985 | Bakalyar | 73/863.72 |
| 4,520,108 A | * | 5/1985 | Yoshida et al. | 436/52 |
| 4,948,565 A | * | 8/1990 | Bemis et al. | 422/103 |
| 5,083,742 A | * | 1/1992 | Wylie et al. | 251/61.1 |
| 5,593,564 A | | 1/1997 | Templin et al. | |
| 5,750,015 A | | 5/1998 | Soane et al. | |
| 5,858,195 A | | 1/1999 | Ramsey | |
| 6,001,229 A | | 12/1999 | Ramsey | |
| 6,010,607 A | | 1/2000 | Ramsey | |
| 6,010,608 A | | 1/2000 | Ramsey | |
| 6,033,546 A | | 3/2000 | Ramsey | |
| 6,090,251 A | | 7/2000 | Sundberg et al. | |

(Continued)

FOREIGN PATENT DOCUMENTS

| | | |
|---|---|---|
| EP | 0620432 | 10/1994 |
| WO | WO98/49548 | 11/1998 |
| WO | WO00/22409 | 4/2000 |
| WO | WO00/65337 | 11/2000 |

*Primary Examiner*—Jill Warden
*Assistant Examiner*—Brian Sines
(74) *Attorney, Agent, or Firm*—Liu & Liu

(57) ABSTRACT

Fixed volumes of samples are metered into the reaction channel of a microfluidic device using one or more slidable blocks having at least one fixed-length sample metering channel. In another aspect of the present invention, fixed volumes of samples are metered into the reaction channel using one or more slidable blocks having at least one fixed-length sample metering channel. In another aspect of the present invention, a sample injection scheme based on injection time is implemented using relatively sliding blocks of separation channels and sample channels. In a further aspect of the present invention, separation channels are configured in relation to the slidable block in a manner that enables separations to be conducted continuously for high-throughput assays.

14 Claims, 10 Drawing Sheets

U.S. PATENT DOCUMENTS

| | | | |
|---|---|---|---|
| 6,096,276 A | * | 8/2000 | Laursen ........................ 422/103 |
| 6,110,343 A | | 8/2000 | Ramsey et al. |
| 6,117,396 A | | 9/2000 | Demers |
| 6,136,269 A | | 10/2000 | Winkler et al. |
| 6,149,787 A | | 11/2000 | Chow et al. |
| 6,235,175 B1 | | 5/2001 | Dubrow et al. |
| 6,280,589 B1 | | 8/2001 | Manz et al. |
| 6,306,273 B1 | | 10/2001 | Wainright et al. |
| 6,306,659 B1 | | 10/2001 | Parce et al. |
| 6,321,791 B1 | | 11/2001 | Chow |
| 6,322,683 B1 | | 11/2001 | Wolk et al. |

* cited by examiner

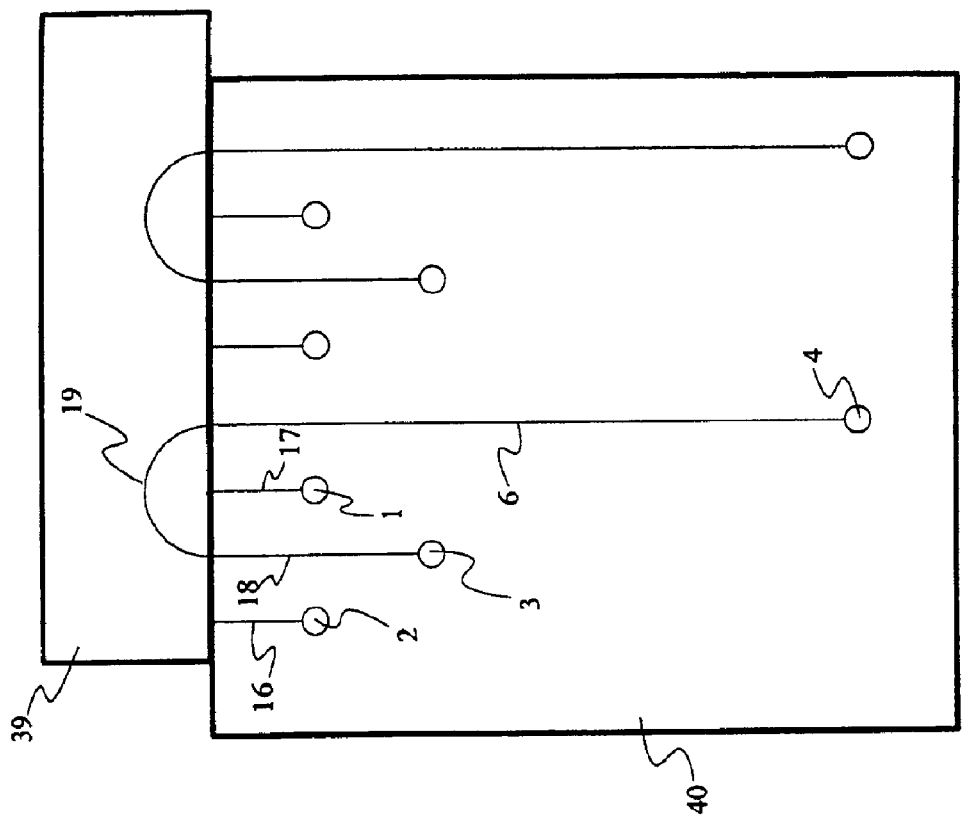
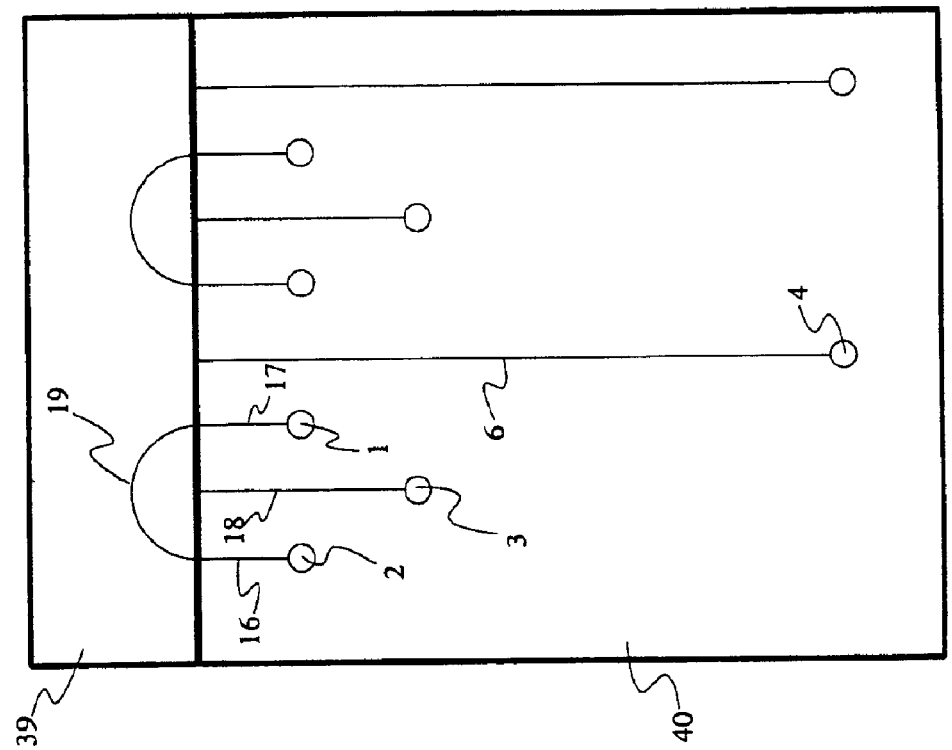

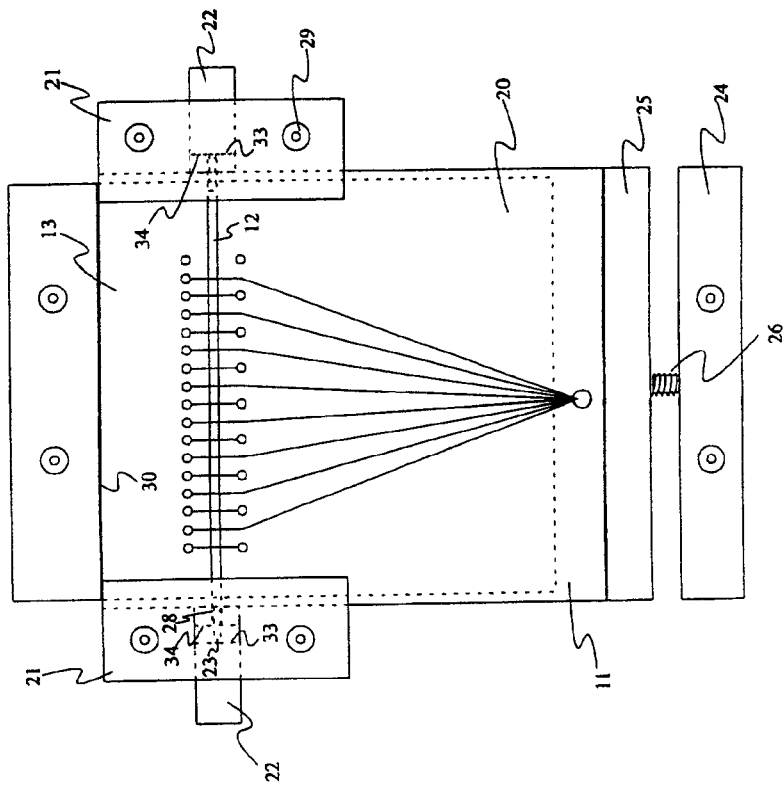
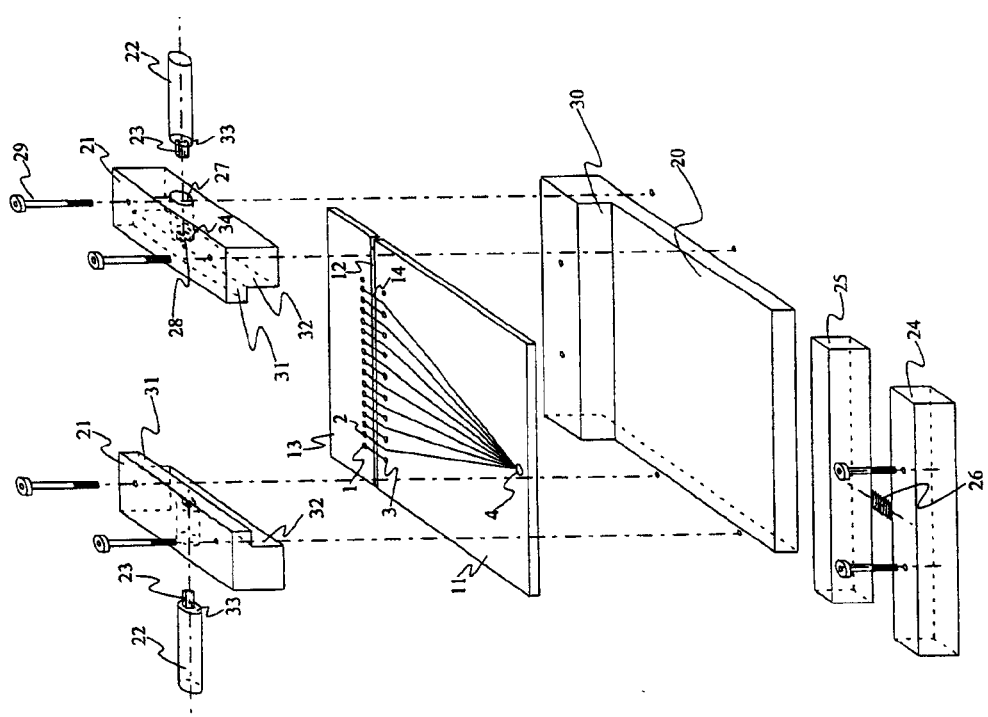
FIG. 9b
FIG. 9a

METHOD AND APPARATUS FOR REPRODUCIBLE SAMPLE INJECTION ON MICROFABRICATED DEVICES

This patent application claims the benefit under 35 U.S.C. § 119(e) of U.S. provisional patent application Ser. No. 60/267,474, filed on Feb. 9, 2001.

BACKGROUND OF THE INVENTION

1. Cross-Reference

U.S. patent application Ser. No. 10/076,042 entitled METHOD AND APPARATUS FOR SAMPLE INJECTION ON MICROFABRICATED DEVICES, concurrently filed on Feb. 11, 2002, which is assigned to MicroChem Solutions, Inc., the assignee of the present invention, and which is fully incorporated by reference herein.

2. Field of the Invention

The present invention relates generally to miniature instrumentation for conducting chemical reaction and/or bio-separation, and diagnostics and/or analysis related thereto, and more particularly, to the introduction of samples to the chemical reaction and/or bio-separation channels in microfabricated devices.

3. Description of Related Art

Bioanalysis, such as DNA analysis, is rapidly making the transition from a purely scientific quest for accuracy to a routine procedure with increased, proven dependability. Medical researchers, pharmacologists, and forensic investigators all use DNA analysis in the pursuit of their tasks. Yet due to the complexity of the equipment that detects and measures DNA samples and the difficulty in preparing the samples, the existing DNA analysis procedures are often time-consuming and expensive. It is therefore desirable to reduce the size, number of parts, and cost of equipment, to make easy sample handling during the process.

One type of DNA analysis instruments separates DNA molecules by relying on electrophoresis. Electrophoresis techniques could be used to separate fragments of DNA for genotyping applications, including human identity testing, expression analysis, pathogen detection, mutation detection, and pharmacogenetics studies. The term electrophoresis refers to the movement of a charged molecule under the influence of an electric field. Electrophoresis can be used to separate molecules of different electrophoretic mobilities in a given separation medium. DNA fragments are one example of such molecules.

There are a variety of commercially available instruments applying electrophoresis to analyze DNA samples. One such type is a multi-lane slab gel electrophoresis instrument, which as the name suggests, uses a slab of gel on which DNA samples are placed. Electric charges are applied across the gel slab, which cause the DNA sample to be separated into DNA fragments of different masses.

Another type of electrophoresis instruments is the capillary electrophoresis instrument. Capillary electrophoresis can be considered as one of the latest and most rapidly expanding techniques in analytical chemistry. Capillary electrophoresis refers to a family of related analytical techniques that uses very strong electric fields to separate molecules within narrow-bore capillaries (typically 20–100 um internal diameter). Capillary electrophoresis techniques are employed in seemingly limitless applications in both industry and academia.

A variety of molecules can be separated by capillary electrophoresis techniques. Sample types include simple organic molecules (charged or neutral), inorganic anions and cations, peptides, oligonucleotides, and DNA sequence fragments. Since the introduction of commercial instrumentation in 1988, the inherent capabilities of capillary electrophoresis and its various modes of operation have been widely demonstrated. Major advantages of capillary electrophoresis include high separation efficiency, small sample and reagent consumption, and low waste generation. The sample fragments in capillary electrophoresis are often analyzed by detecting light emission (e.g., from radiation induced fluorescence) or light absorption associated with the sample. The intensities of the emission are representative of the concentration, amount and/or size of the components of the sample.

Specifically, in capillary electrophoresis, separation is performed in small capillary tubes to reduce band broadening effects due to thermal convection and hence improve resolving power. By applying electrophoresis in a capillary column carrying a buffer solution, the sample size requirement is significantly smaller and the speed of separation and resolution can be increased multiple times compared to the slab gel-electrophoresis method. Only minute volumes of sample materials, typically less than 20 nanoliters, are required to be introduced into the separation capillary column.

It was mentioned in The Journal of Chromatography, 452, (1988) 615–622, that sample valves are the most suitable sampling method for capillary electrophoresis. The limitation of this method is the large sampling volume. A rotary injection valve has been used in capillary electrophoresis with a sampling volume of 350 nanoliters. The results have been reported in Anal. Chem. 59, (1987) 799. This volume is too large to be used for high-resolution separations. Later, an internal loop injection valve with an injection loop volume of $\geq 20$ nL has become commercially available, but connecting capillaries to this valve is too much of a challenge and consequently it is not often used in capillary electrophoresis.

Current practical techniques for sample injection in capillary electrophoresis include electromigration and siphoning of sample from a container into one end of a separation column. For the siphoning injection technique, the sample reservoir is coupled to the inlet end of the capillary column and is raised above the buffer reservoir that is at the exit end of the capillary column for a fixed length of time. The electromigration injection technique is effected by applying an appropriate polarized electrical potential across the capillary column for a given duration while the entrance end of the capillary is in the sample reservoir. For both sample injection techniques the input end of the analysis capillary tube must be transferred from a sample reservoir to a buffer reservoir to perform separation. Thus, a mechanical manipulation is involved. It is also difficult to maintain consistency in injecting a fixed volume of sample by either of these techniques, as the sample volume injected are susceptible to changes in sample viscosity, temperature, etc., thereby resulting in relatively poor reproducibility in injected sample volumes between separation runs. Electromigration additionally suffers from electrophoretic mobility-based bias.

Electrophoresis based on microfabricated chips possesses many unique advantages over conventional capillary electrophoresis. One of them is the so-called "differential concentration" effect for separation of DNA sequencing fragments. For sequencing using conventional capillary gel electrophoresis, the signal intensity of separated fragment has an exponential profile against fragment size. That is, very high signal intensities for short fragments and very low for large fragments. Often, the readlength of DNA sequencing is limited by the low signal intensity rather than the resolution for the long fragments. This exponential profile also requires a wide dynamic range for detection.

Capillary electrophoresis on microchips is an emerging new technology that promises to lead the next revolution in chemical analysis. It has the potential to simultaneously assay hundreds of samples in minutes or less time. Microfluidic chips used in electrophoretic separations usually have dimensions from millimeters to decimeters. The largest electrophoretic separation chip so far has a substrate having dimensions of 50-cm×25-cm, which was disclosed in Micro Total Analysis Systems 2001, 16–18. These microfluidic platforms require only nanoliter or picoliters volumes of sample, in contrast to the microliter volumes required by other separation technologies. These samples may potentially be prepared on-chip for a complete integration of sample preparation and analysis functions. The rapid analysis combined with massively parallel analysis arrays could yield ultrahigh throughputs. These features make microchips an attractive technology for the next generation of capillary electrophoresis instrumentation.

These microchips are prepared using microfabrication techniques developed in the semiconductor industry. Capillary channels are fabricated in microchips using, for example, photolithography or micromolding techniques. Microchips have been demonstrated for separations of amino acids, DNA restriction fragments, PCR products, short oligonucleotides, and sequencing ladders.

For capillary electrophoresis separation on microchips, samples are usually introduced using either cross-channel or double-T sample injectors. The cross-channel injector has been disclosed in U.S. Pat. No. 6,001,229. As illustrated in FIG. 1a, the cross-channel injector is formed by orthogonally intersecting the separation-channel 6 with a cross-channel 5 and 5a connecting the sample reservoir 1 to an analyte waste reservoir 2. To load sample to the separation-channel 6, analytes are electrophoresed (e.g., by electrokinetic forces) from the sample reservoir 1 to the analyte waste reservoir 2, filling the whole cross-channel 5 including the intersection region 7. When an electric potential is applied to cathode reservoir 3 and anode reservoir 4 along the separation-channel 6 after analytes have been loaded into the intersection region 7, the analytes residing in the intersection region 7 are electrokinetically driven down the separation-channel 6 to perform electrophoretic separation.

In the sample loading process, as analytes migrate across the intersection region 7 analytes disperse orthogonally into the separation-channel 6 due to the electric field distortion and molecular diffusion. This degrades the resolving power and makes the separation irreproducible. To overcome this dispersion, selected voltages are applied to the cathode and anode reservoirs 3 and 4 such that buffer electrolytes, along with the dispersed analytes, are electrokinetically driven to the intersection region 7 and ultimately to the analyte waste reservoir 2. Therefore analyte dispersion is suppressed. This is called a "pinched" injection mode.

A double-T injector on microchips has been disclosed in U.S. Pat. No. 6,280,589. In a double-T injector (referring to FIG. 1b), the sample channel across the separation channel 6 is divided by the separation-channel into two segments 8 and 9 that are offset by a given distance along the separation channel 6. If the channel connecting the sample reservoir 1 and analyte waste reservoir 2 is still considered the "cross-channel", the offset segment 10 is shared by the "cross-channel" and the separation-channel 6. Similar to the cross-channel injector in FIG. 1a, sample is loaded by electrophoresis, from the sample reservoir 1 to the analyte waste reservoir 2, filling the cross-channel segments 8 and 9 and the offset segment 10. As an electric potential is applied to cathode and anode reservoirs 3 and 4 across the separation-channel 6 (including the offset segment 10) after analytes have been loaded in the off-set segment 10, the analytes residing in the offset segment region 10 are electrokinetically driven down the separation-channel 6 to perform electrophoretic separation. Double-T injectors also suffer from dispersion of analytes into the separation channel. "Pinched" injection mode is usually used to suppress this problem, as discussed in Anal. Chem. 71 (1999) 566–573.

Precise control of the potentials on multiple electrodes in reservoirs 1, 2, 3 and 4 is critical to achieving desired and reproducible results for either cross-channel or double-T injectors, especially when a "pinched" injection mode is employed. These potentials are balanced and calibrated normally using a standard sample until reproducible results have been obtained. However, when samples of different ionic strength and viscosity are to be analyzed, that calibrated potential balance for the device is no longer applicable, and consequently giving rise to undesired and/or irreproducible results.

For sequencing separation on chips with a cross or a double-T sample injector, a uniform signal intensity profile is typically obtained. The mechanism has been illustrated in the Proc. Natl. Acad. Sci. U.S.A. 97 (2000) 5369–5374. During injection, sample is electrophoresed through the cross channel to the offset segment 10 (referring to FIG. 1b). This electrophoresis of DNA fragments provides differential enrichment of sequencing fragments. Little change in concentration will occur at the sample/gel interface for small DNA fragments and inorganic ions because their electrophoretic mobilities are similar in free solution and in sieving matrix. On the other hand, a considerable increase in the steady-state concentration will occur at the sample/gel interface for the large fragments because of their reduced mobility in the gel. These results in a concentration compensation for large fragments. Concentrations of large fragments are always lower than those of small fragments in a typical sequencing sample. A uniform intensity profile is therefore generated.

Another advantage of microchips is to use cross-channel 5 or 8 (referring to FIG. 1) to perform sample preseparation or cleanup. Taking DNA sequencing for example, when sample is electrophoresed through the cross channel 5 to the intersection region 7 or segment 8 to the offset segment 10, at an optimized injection time, the majority of the fragments have reached a steady-state concentration in the intersection region 7 or segment 10, while large template and enzyme molecules are still migrating in the cross channel 5 or 8. When voltages are switched to separation, only the fragments in the injector are injected into the separation channel during the separation, while DNA template and enzyme contaminants were removed from the separation channel. Removal of these large molecules has been reported essential to achieve high quality separations. In capillary gel electrophoresis (CGE), they are removed using offline membrane filters.

T-injectors may be used for sample introduction on microchips as well. In this scheme (referring to FIG. 1c), the analyte waste reservoir 2 and the channel 9 between the separation-channel 6 and analyte waste reservoir 2 in FIG. 1b are eliminated. Analytes are electrophoresed from the sample reservoir 1 through the half "cross-channel" 8 directly into the separation-channel 6. Since the other half of the "cross-channel" 9 is omitted, all analytes exit the half "cross-channel" 8 enter and build up in the separation-channel 6 as the sample loading process continues.

However, there are two major problems associated with the T-injector. The first problem is the augmented electrophoretic mobility-based bias. In a normal electrokinetic injection process of capillary electrophoresis, as the sample inlet end of a separation capillary is dipped directly into the sample solution and all analytes migrate into the separation capillary simultaneously, the electrophoretic mobility-based bias equals to the ratio of their electrophoretic mobilities. In this T-injection scheme, the sample reservoir 1 and the inlet end of the separation-channel 6 are separated by the half "cross-channel" 8. Fast-moving analytes have already migrated into the separation-channel 6 when slow-moving analytes are still migrating in the half "cross-channel" 8. As a result, fast-moving analytes are more preferentially introduced in T-injectors than in conventional capillary electrophoresis and therefore the electrophoretic mobility-based bias is augmented.

The second problem is the difficulty in precisely controlling a finite amount of analytes into the separation-channel 6. This problem is associated with the variation of length of the half "cross-channel" 8. In a microchip fabrication process, channels are photolithographically created and can be very precisely arranged. The reservoirs are holes drilled or physically attached and their positions and dimensions cannot be reproducibly and precisely produced. In T-injection schemes, the quantity of the analytes injected into the separation-channel 6 is normally controlled through timing of the applied electrical potential. Because analytes going to the separation-channel 6 have to pass through the half "cross-channel" 8, it is a significant challenge to attempt to control the timing so that only a given finite amount of analytes is allowed to migrate into the separation-channel 6. Variation of the length of this channel makes the problem even more challenging.

It is therefore desirable to develop a robust, reproducible and automated sample injection scheme for a microfabricated device, which would overcome the limitations in the prior art.

SUMMARY OF THE INVENTION

The present invention provides a simplified, accurate and reproducible fixed volume sample injection scheme for introducing samples from sample reservoirs into microchannels for separation, chemical reaction, etc. (generally referred to as reaction channels or columns) in microfabricated devices, which overcomes the drawback of the prior art. The sample introduction schemes can be used for variety of applications, including integrated microfluidic systems for chemical analysis and sensing, and analytical separation techniques such as capillary electrophoresis, capillary electrochromatography, microcolumn liquid chromatography, flow injection analysis, and field-flow fractionation.

In one aspect of the present invention, fixed volumes of samples are metered into the reaction channel using one or more slidable blocks having at least one fixed-length sample metering channel. In one embodiment, the sample injection scheme comprises three blocks, in which at least one block has a fixed-length sample metering channel and is slidable relative to a block having a separation channel. In another embodiment, the sample injection scheme comprises two blocks for implementing fixed-volume sample injection.

In another aspect of the present invention, a sample injection scheme based on injection time is implemented using relatively sliding blocks of separation channels and sample channels.

In a further aspect of the present invention, separation channels are configured in relation to the slidable block in a manner that enables separations to be conducted continuously for high-throughput assays. In one embodiment, continuous separation is implemented comprising three blocks in which at least one block is slidable relative to the other blocks. In another embodiment, continuous separation is implemented comprising two relatively slidable blocks.

In accordance with the sample injection schemes of the present invention, it is not required to balance multiple potentials during the process of sample introduction and/or sample separation. Very small fixed-volume sample injection is achieved. The reproducibility of sample volume injected into the reaction channel is improved. A wide quantity range of analytes can be injected into the reaction channel. The present invention also takes advantage of "differential concentration" effect.

The operations of the various embodiments of the present invention are controlled by a controller (not shown) to accomplish the functions recited herein.

Other objects, advantages and salient features of the invention will become apparent to those persons skilled in the art upon reading the following detailed description, which taken in conjunction with the annexed drawings, disclosed preferred embodiments of the invention.

BRIEF DESCRIPTION OF THE DRAWINGS

FIGS. 8a–8b are schematic representations of another alternative two-piece fixed-volume-injector in which all reservoirs are located on a non-moving part of the chip in accordance with another embodiment of the present invention;

FIGS. 9a–9b are schematic representations of an injector holder assembly to perform automatic sample injection in accordance with one embodiment of the present invention.

DETAILED DESCRIPTION OF THE ILLUSTRATED EMBODIMENTS

The present description is of the best presently contemplated mode of carrying out the invention. This description is made for the purpose of illustrating the general principles of the invention and should not be taken in a limiting sense. The scope of the invention is best determined by reference to the appended claims.

For purpose of illustrating the principles of the present invention and not limitation, the present invention is described by reference to embodiments directed to separation in capillary electrophoresis. The present invention is equally applicable to chemical reactions, diagnostics and/or analysis in microfluidic devices. All references to separation channel hereinafter are examples of reaction channels, and are equally applicable to channels for other purposes in microfluidic devices.

Microfabricated electrophoresis chips possess many unique advantages over conventional capillary electrophoresis. One of them is the so-called "differential concentration" effect for separation of DNA sequencing fragments.

For sequencing using conventional capillary gel electrophoresis, the signal intensity of separated fragment has an exponential profile against fragment size. That is, very high signal intensities for short fragments and very low for large fragments. Often, the readlength of DNA sequencing is limited by the low signal intensity rather than the resolution for the long fragments. This exponential profile also requires a wide dynamic range for detection.

Figure 1A:
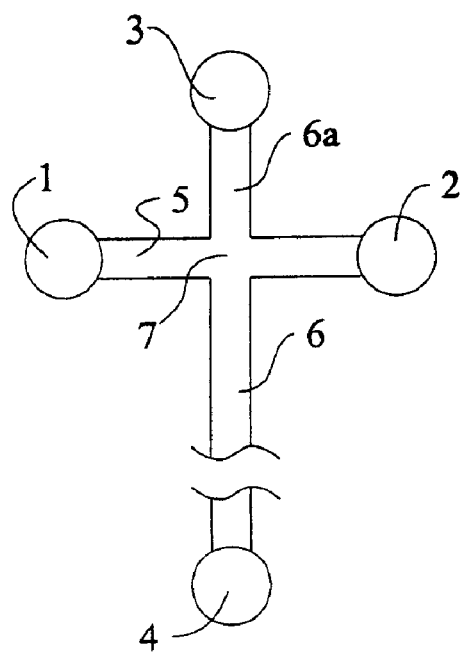
FIGS. 1a–1c are schematic representations of prior art injection schemes on chips.

For sequencing separation on chips with a cross or a double-T injector, a uniform signal intensity profile is typically obtained. The mechanism has been illustrated in the Proc. Natl. Acad. Sci. U.S.A. 97 (2000) 5369–5374. During injection, sample is electrophoresed through the cross channel to the intersection region 7 (referring to FIG. 1a). This electrophoresis of DNA fragments provides differential enrichment of sequencing fragments. Little change in concentration will occur at the sample/gel interface for small DNA fragments and inorganic ions because their electrophoretic mobilities are similar in free solution and in sieving matrix. On the other hand, a considerable increase in the steady-state concentration will occur at the sample/gel interface for the large fragments because of their reduced mobility in the gel. These results in a concentration compensation for large fragments, concentrations of large fragments are always lower than those of small fragments in a typical sequencing sample. A uniform intensity profile is therefore generated.

Figure 1B:
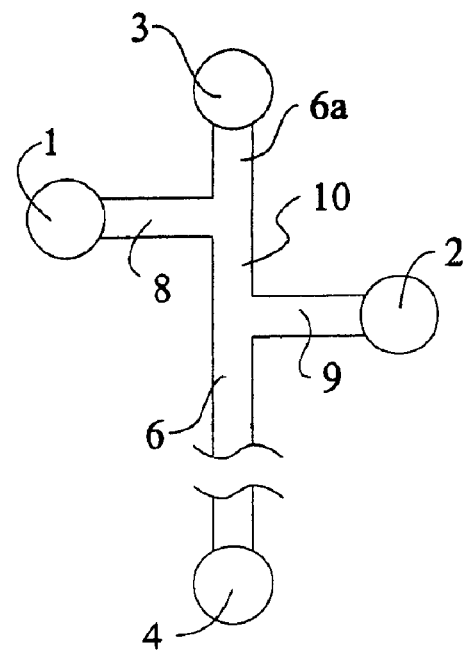
Figure 1C:
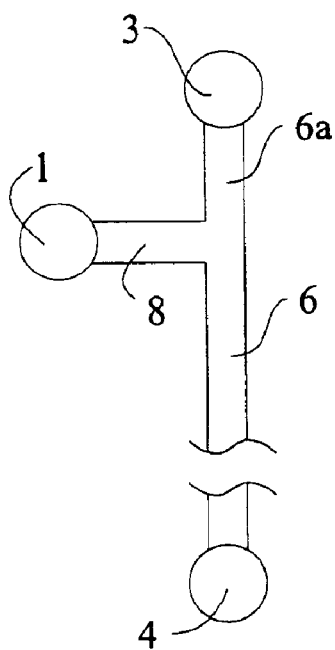

Another advantage of microchips is to use cross-channel 5 or 8 (referring to FIG. 1) to perform sample preseparation or cleanup. Taking DNA sequencing for example, when sample is electrophoresed through the cross channel 5 or 8 to the intersection region 7, at an optimized injection time, the majority of the fragments have reached a steady-state concentration in the intersection region 7 while large template and enzyme molecules are still migrating in the cross channel 5 or 8. When voltages are switched to separation, only the fragments in the injector are injected into the separation channel during the separation, while DNA template and enzyme contaminants were removed from the separation channel. Removal of these large molecules has been reported essential to achieve high quality separations. In capillary gel electrophoresis (CGE), they are removed using offline membrane filters.

Microfluidic chips used in electrophoretic separations usually have dimensions from millimeters to decimeters. The largest electrophoretic separation chip so far has dimensions of 50-cm×25-cm, which was disclosed in Micro Total Analysis Systems 2001, 16–18. These microfluidic platforms require only nanoliter volumes of sample, in contrast to the microliter volumes required by other separation technologies. So far, it is desirable a robust, reproducible and automated sample injection scheme for practical microfluidic systems. Interfacing microfluidic channels with real-world sample and reagent solutions is another challenging issue to be addressed before realizing the full benefit of microfluidic systems. Sample injection valves are considered the most suitable sampling method for capillary electrophoresis because they introduced fixed volumes of samples, and hence reproducible and reliable. Problems of using commercially available valves on chips are their large injection volumes and difficulties in incorporating capillary channels with the valves. The present invention solves these long-standing problems by introducing several fixed-volume injectors with a wide range of injection volumes, especially small volumes. These injectors and separation channels are well integrated in a single device.

Figure 2C:
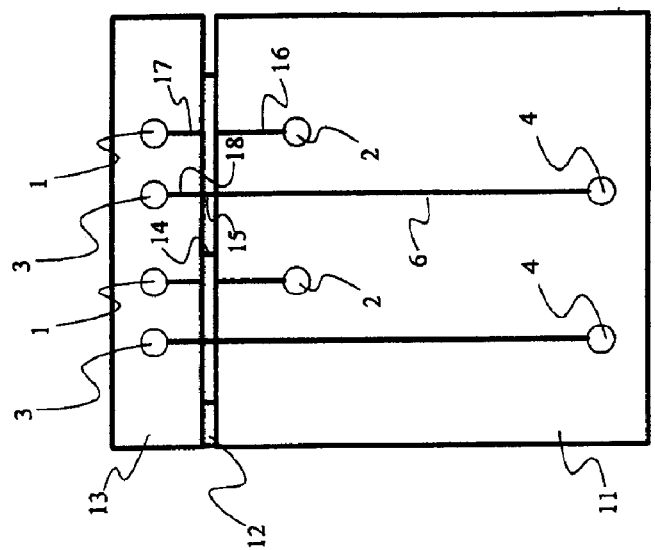
FIGS. 2a–2c are schematic representations of a three-piece fixed-volume-injector according to one embodiment of the present invention.
Figure 2B:
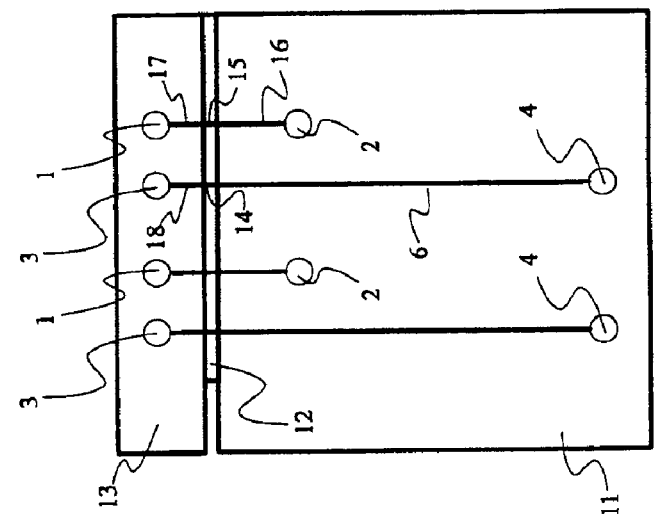
Figure 2A:
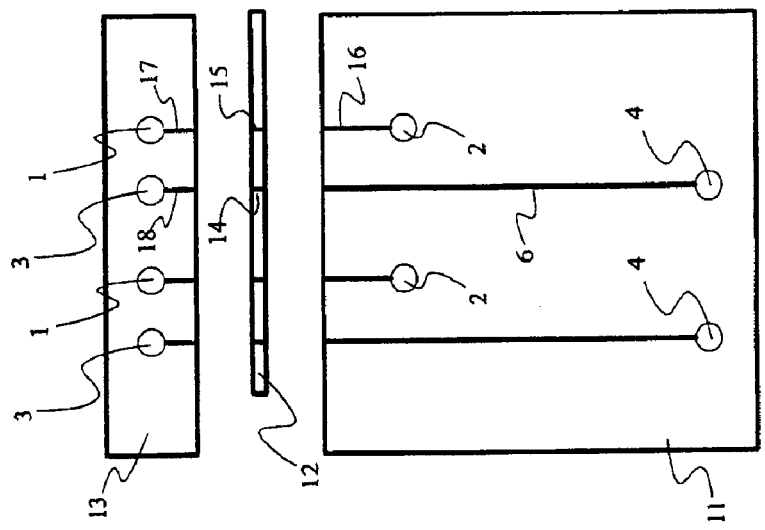

In a particular preferred embodiments, referring to FIG. 2a, the fixed-volume-injector of the present invention is configured in a structure that comprises a separation-channel body 11, injection bar 12, and sample-reservoir body 13. The separation-channel body 11 contains waste reservoirs 2 and anode reservoirs 4. The injection bar defines channels for sample injectors 15 and auxiliary channels 14. The sample-reservoir body includes sample reservoirs 1, cathode reservoirs 3 and their corresponding channels 17 and 18.

FIG. 2b shows the relative positions of the separation-channel body 11, injection bar 12, and sample-reservoir body 13 at the start stage of sample loading into the injector channels on the injection bar. During operation, sample reservoirs 1 are loaded with different samples. When a proper voltage is applied between sample reservoirs 1 and analytes waste reservoirs 2, analytes in the sample reservoirs 1 electrophoretically migrate, through the injectors 15, to the waste reservoirs 2. Then, the injection bar 12 is switched to the position as shown in FIG. 2c by sliding the injection bar 12, where cathode channels 18, injectors 15 and separation channels 6 are all well aligned. A proper separation voltage is then applied between cathode reservoirs 3 and anode reservoirs 4 to introduce the analytes from the injectors 15 to separation channel 6 for analysis. After separation is completed, the injection bar 12 is switched back to its original position for analysis of the next samples. In this example, both separation channels 6 can run in parallel.

In the process of sample introduction and separation, no "pinched" injection mode is used and potentials applied to reservoirs don't need to be balanced. Channel 17 may also be used to take advantage of the "differential concentration" effect and perform extra sample cleanup at the stage shown in FIG. 2b.

In preferred embodiments, electric potential gradient along the sliding interfaces is suppressed, more preferably eliminated. The goal is to prevent analytes from electrokinetically moving from one channel to the other along the interfaces. This may be achieved by making channels of the same kind the same length and applying to the reservoirs of the same kind the same voltage.

In other embodiments, the separation-channel body 11, injection bar 12, and sample-reservoir body 13 is made of the same material such as glass, polycarbonates, and poly (methyl methacrylate). For example, a single chip is fabricated first and then it is diced into three parts. Alignments of appropriate channels will be relatively easy since they are originated from the same piece of the chip.

In additional embodiments, the separation-channel body 11, injection bar 12, and sample-reservoir body 13 may be made of different materials. For example, when the injection bar 12 is desired to be thin, polymeric and metallic materials may be used to provide sufficient structural integrity and strength for the intended mechanical movements. When metallic materials are used, the surface of the injector region may be coated with an electrically insulating layer. Alternatively, pieces of insulating materials containing injectors 15 and auxiliary channels 14 may be inserted into a metallic or polymeric frame, and the assembly is used for the injection bar 12.

It can be appreciated that the method and apparatus described in FIG. 2 provides a fixed-volume injection scheme. The dimensions of the channels in the injectors 15 determine the injection volume. When tough material such as metallic foil or polymeric sheet is used, the injection bar may be as thin as 100–500 $\mu$m. Channel of 1-$\mu$m-deep and 1-$\mu$m-wide may be readily fabricated using current photolithographic technologies. This gives an injection volume of 0.1–0.5 picoliter. These dimensions may certainly be further reduced when necessary. For a 100 pM sample solution, this injection volume means an injection of a few molecules into the separation channel.

Material of the same kind such as glass, polycarbonates, and poly(methyl methacrylate) may be used for the separation-channel body 11, injection bar 12, and sample-reservoir body 13. The injection bar usually has a thickness of 500 $\mu$m to 50 mm. Injector channel usually has a depth between 5 $\mu$m to 500 $\mu$m and a width between 10 $\mu$m to 1 mm. This gives a volume range of 25 picoliters to 25 microliters.

Figure 3B:
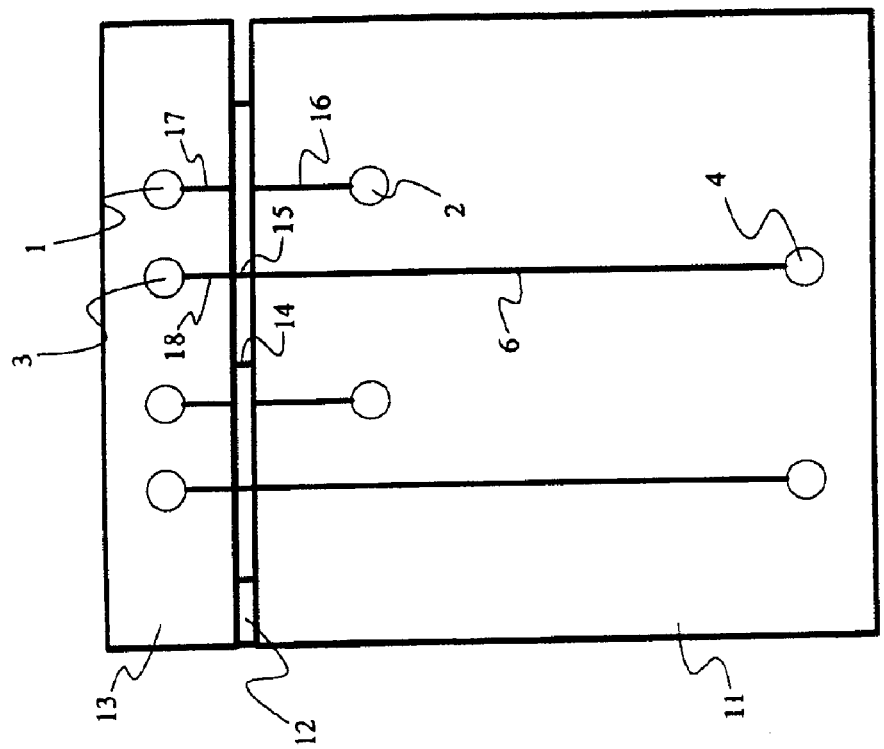
FIGS. 3a–3b are schematic representations of an alternative method to realize sample injection in accordance with another embodiment of the present invention.
Figure 3A:
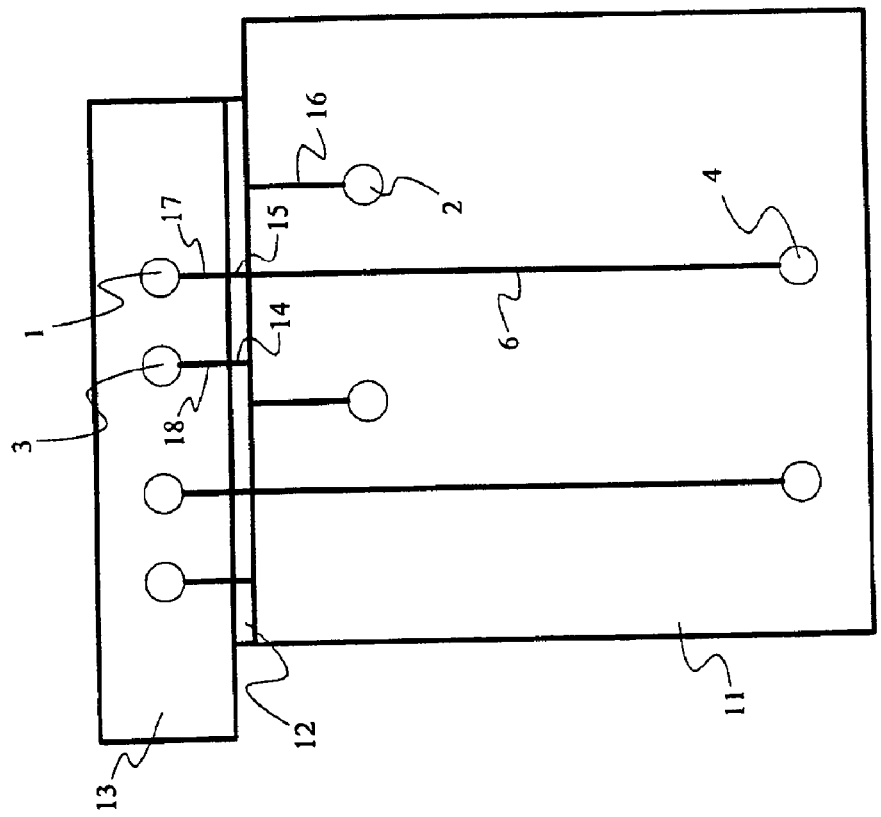

The injection bar may be deformed or broken during the process of sliding back and forth, especially when it is thin. In preferred embodiments (referring to FIG. 3), one way to reduce this deformation or breakage is to slide the injection bar 12 with the sample-reservoir body 13 to the sample injection position (see FIG. 3a), then allow the injection bar stay with the separation-channel body 11 and slide the sample-reservoir body 13 back (see FIG. 3b). To get the injection bar 12 back for sample loading, the sample-reservoir body 13 is moved to the position as shown in FIG. 3a and then both the injection bar 12 and sample-reservoir body 13 are moved back to its original position (see FIG. 2b). A two-step process is needed to move the injection bar 12 from sample loading position to sample injection position, but in each moving step there is only one sliding interface.

Figure 10:
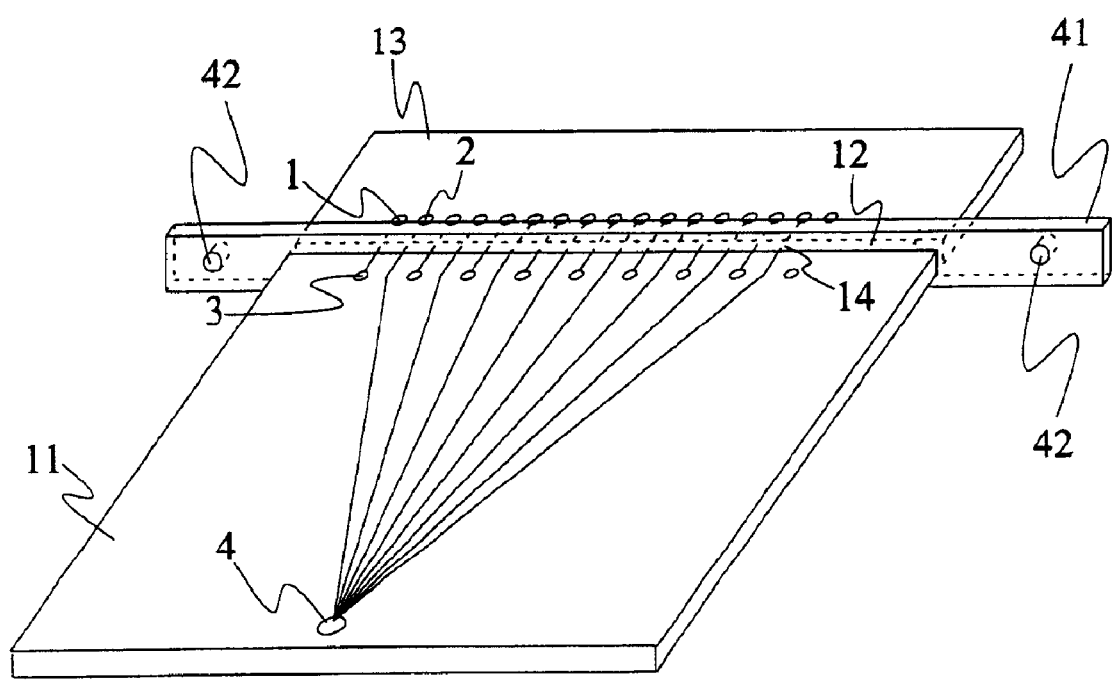
FIG. 10 is a schematic representation of the implementation of protective frame for the injection bar in accordance with one embodiment of the present invention.

In the embodiment shown in FIG. 10, a frame 41 may be used to protect the injection bar when it is very thin. This frame supports the injection bar 12 on its sides, which also facilitates sliding motion of the injection bar back and forth. The holes 42 are used to facilitate the push and/or pull actions and may also be used for proper alignment.

Figure 4B:
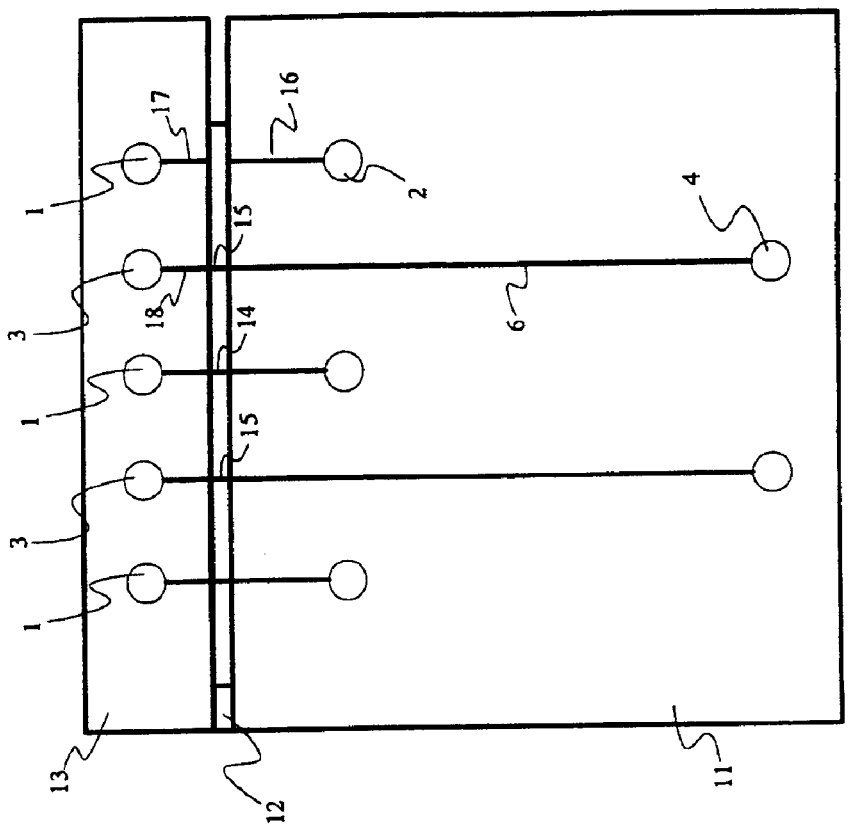
FIGS. 4a–4b are schematic representations of a three-piece fixed-volume-injector in which all separation channels perform separations continuously in accordance with another embodiment of the present invention.
Figure 4A:
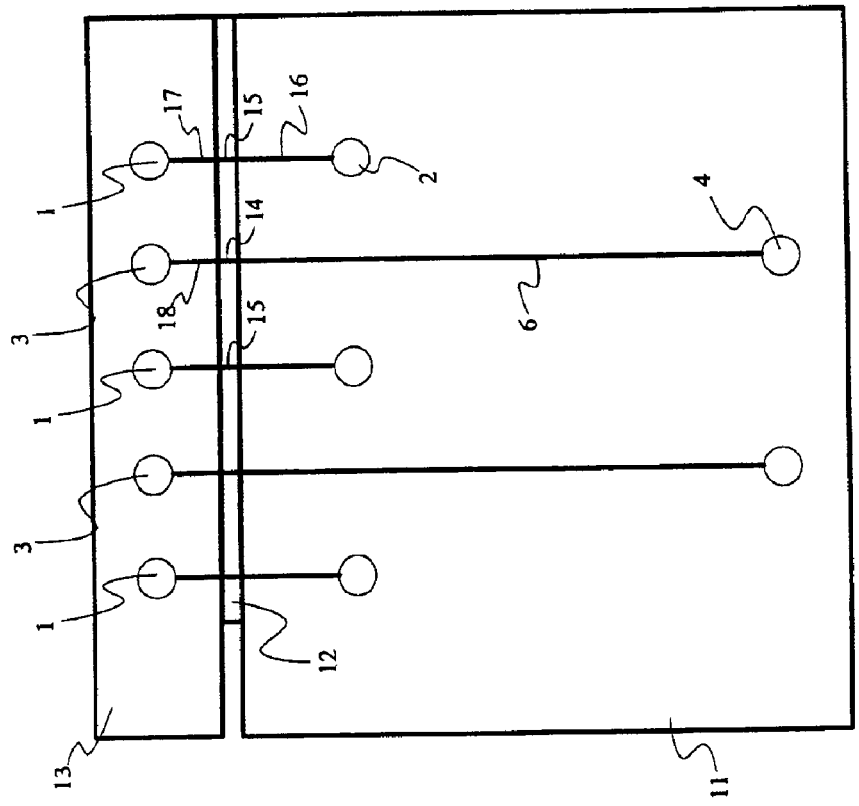

In other preferred embodiments, the fixed-volume-injector is designed as illustrated in FIG. 4. One extra sample and waste reservoirs are fabricated and all channels are equally spaced. In this example, there are three pairs of sample and waste reservoirs and two separation channels 6. After one set of samples is loaded in the two injectors 15 on the right of FIG. 4a, the injection bar 12 is shifted to sample injection position as indicated in FIG. 4b for sample injection. While this set of samples is being separated in the separation channels 6, another set of samples is loaded in the auxiliary channels 14 on the left of FIG. 4b. As the injection bar 12 is shifted back to FIG. 4a, the set of samples in the two auxiliary channels 14 is injected for separation. The set of two auxiliary channels 14 serves as another set of injectors 15. In every movement of the injection bar 12, separation of a new set of samples is performed.

It is within the scope and spirit of the present invention to configure the injector and auxiliary channels in a circle or cylindrical configuration about an axis of rotation (not shown), to create a rotary valve like a conventional sandwich rotary valve. The extra sample and waste reservoirs are not "extra" any more. All channels are effectively utilized in a repetitive cyclic configuration.

Figure 5C:
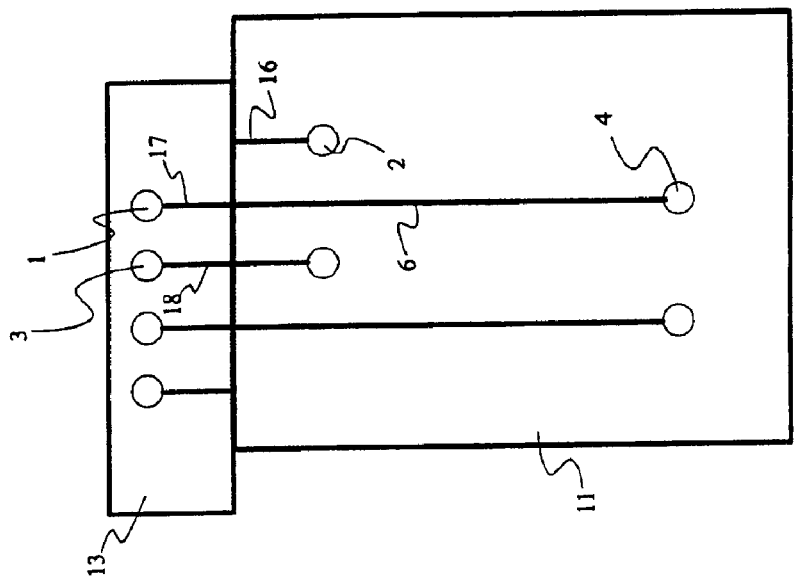
FIGS. 5a–5c are schematic representations of a two-piece fixed-volume-injector in accordance with yet another embodiment of the present invention, which can also be used for fixed-time injection.
Figure 5B:
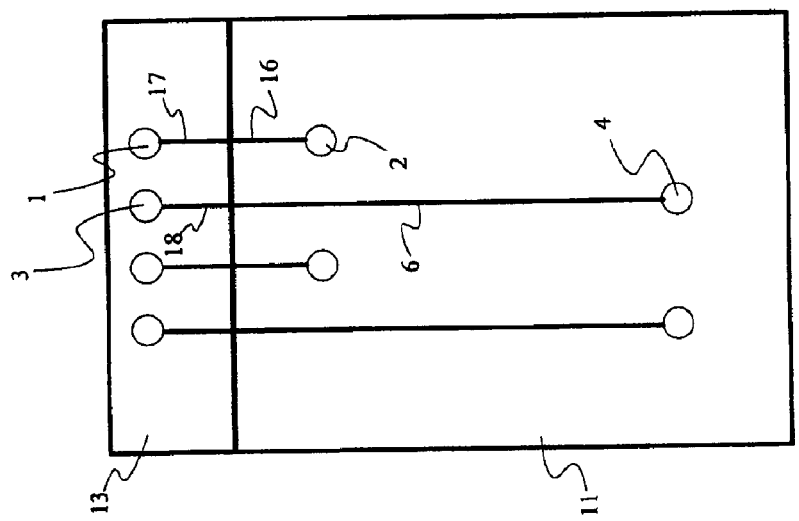
Figure 5A:
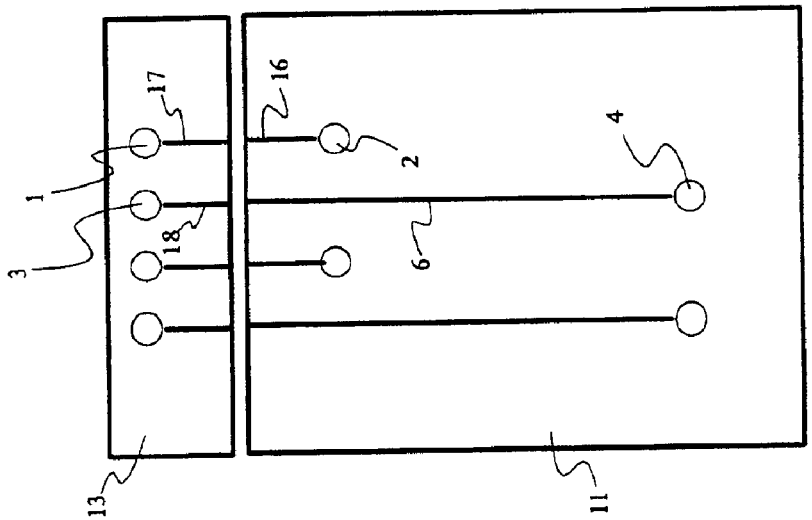

In another embodiment of the present invention, the fixed-volume-injector takes on a structure that comprises two relatively sliding blocks, the sample-reservoir body 13 and the separation-channel body 11 as shown in FIG. 5a. The dedicate injection bar 12 in the previous embodiment is eliminated in this embodiment. In this embodiment, the injector may be operated in one of the two modes: timed injection mode and fixed-volume injection mode. In a timed injection mode, referring to FIG. 5b, samples are loaded in the sample reservoirs 1 and electrophoresed across channels 17 and 16 to waste reservoirs 2. Then, the sample-reservoir body 13 is shifted to a sample injection position as shown in FIG. 5c. A sample injection voltage is applied briefly between sample reservoirs 1 and anode reservoirs 4. The quantity of analytes injected is controlled mainly by the time in which this sample injection voltage is applied. After sample injection, the sample-reservoir body 13 is shifted back to the configuration is shown in FIG. 5b, and a separation voltage is applied between cathode reservoirs 3 and anode reservoirs 4 for separation.

In a fixed-volume injection mode, in the configuration shown in FIG. 5b, samples are loaded in sample reservoirs 1 and electrophoresed across channels 17 and 16 to waste reservoirs 2. Thereafter, the sample reservoirs 1 are cleaned and loaded with electrophoresis buffer. The sample-reservoir body 13 is shifted to sample injection position as shown in FIG. 5c. Then an injection voltage is applied between sample reservoirs 1 and anode reservoirs 4 to inject all the analytes in channel 17 to the separation channel 6. The sample-reservoir body 13 is then shifted back to its original position as shown in FIG. 5b. A separation voltage is applied between cathode reservoirs 3 and anode reservoirs 4 for separation. The amount of analytes injected is determined by the size of channel 17. The length of channel 17 is preferably longer than 1 mm, more preferably longer than 3 mm, to ensure good reproducibility.

Figure 6B:
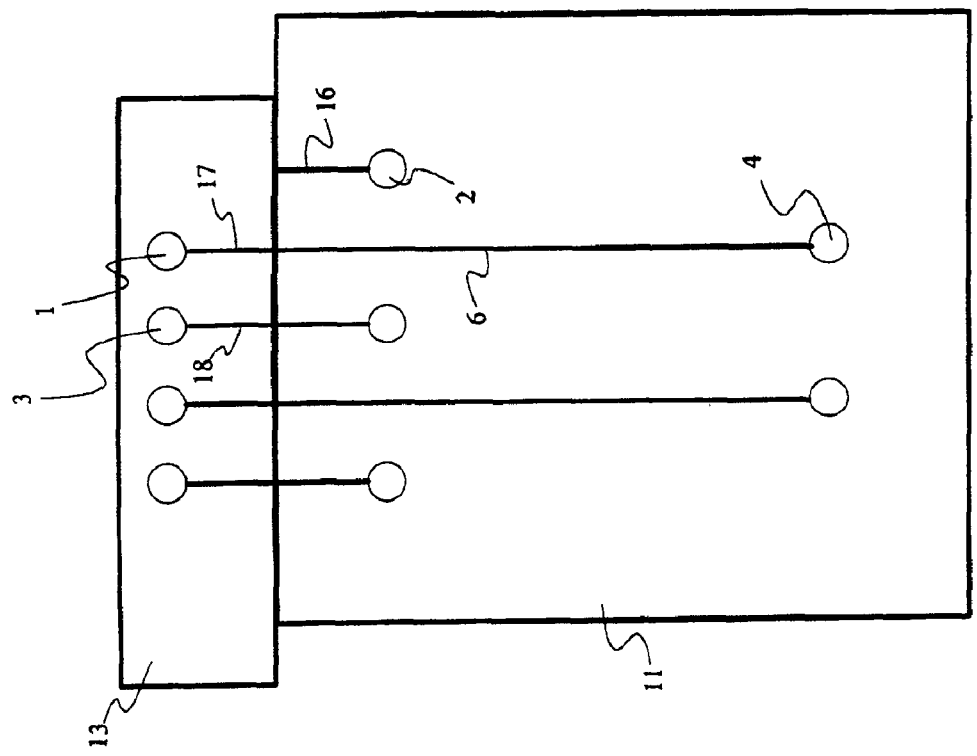
FIGS. 6a–6b are schematic representations of a two-piece fixed-volume-injector in which all separation channels perform separations continuously in accordance with a further embodiment of the present invention.
Figure 6A:
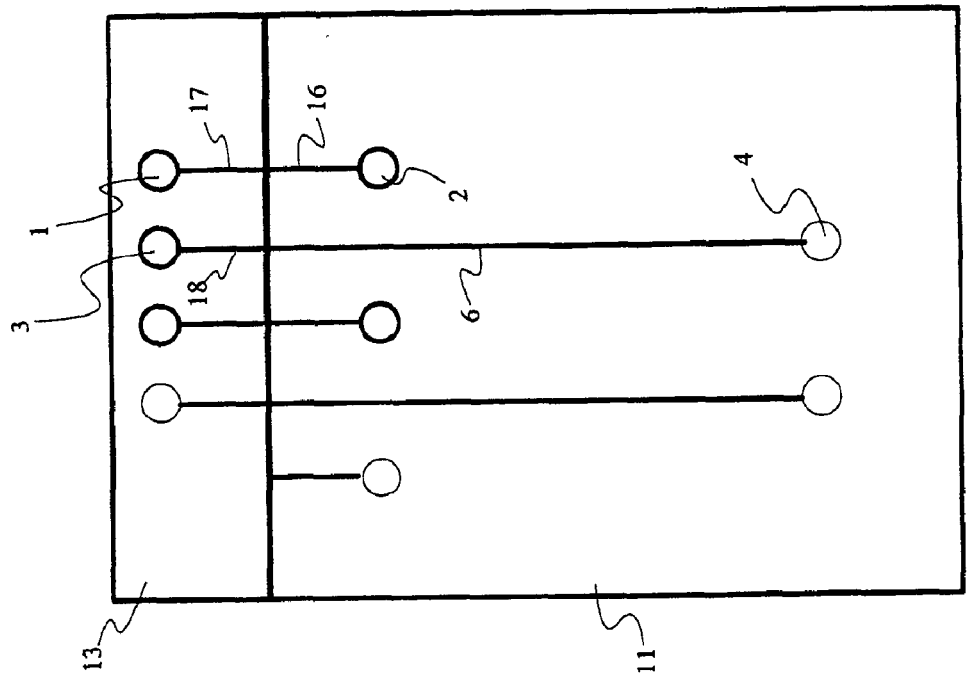
Figure 7C:
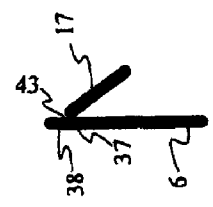
FIGS. 7a–7d are schematic representations of a two-piece fixed-volume-injector in accordance with an alternate embodiment of the present invention.
Figure 7D:
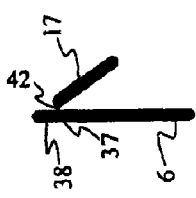
Figure 7B:
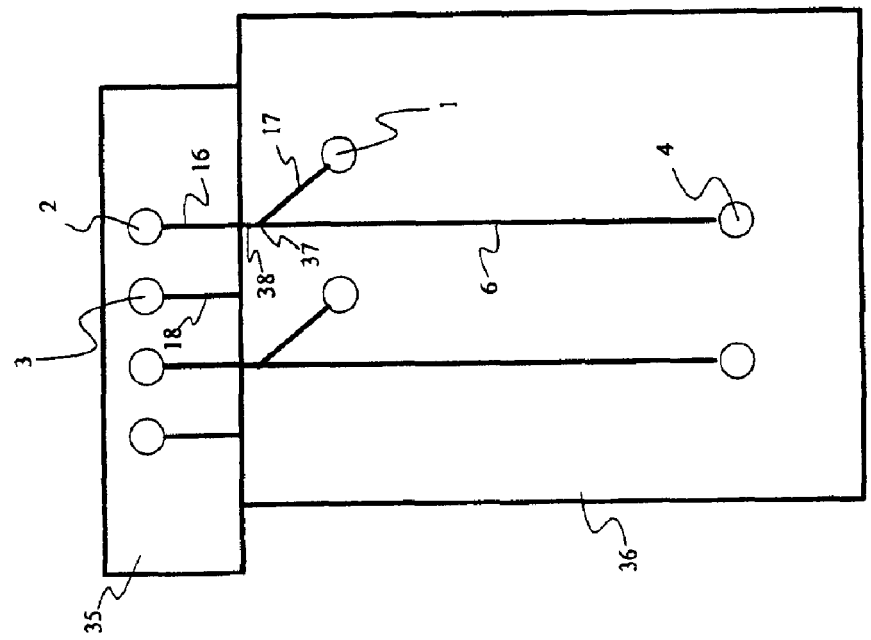
Figure 7A:
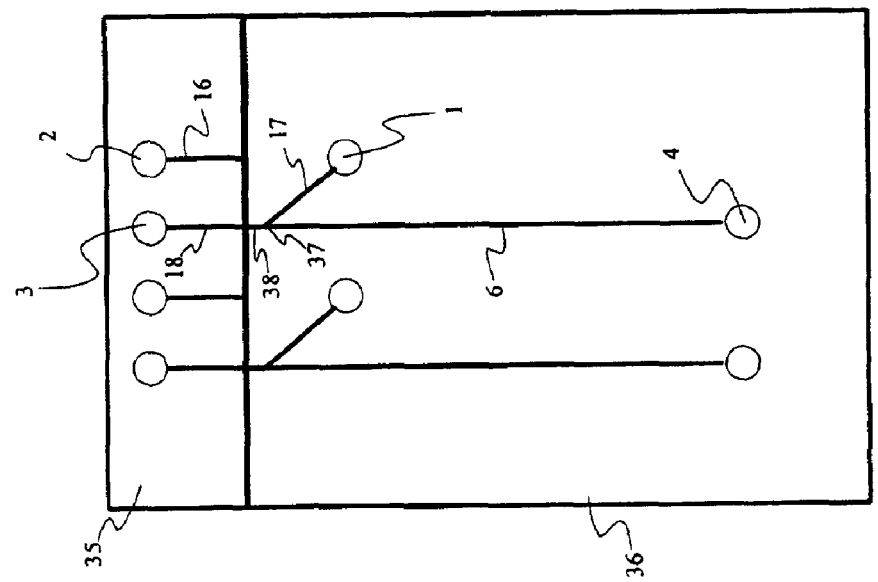

In a further embodiment, the chip in FIG. 5 is slightly modified to contain an extra waste analyte reservoir 2 and channel 16 as illustrated in FIG. 6. The sample is metered into channel 17 (FIG. 6a) as in the previous embodiment in FIG. 5b. After the first set of samples is injected in FIG. 6b, the sample-reservoir body 13 stays in sample injection position as shown in FIG. 6b to perform sample separation. Sample injection and separation may be combined into a single step. While this set of sample is in the process of separation, another set of samples is loaded in the cathode reservoirs 3, electrophoresed across channel 18 and 16 to waste analyte reservoirs 2. Then the samples in cathode reservoirs are cleaned and electrophoresis buffer solution is introduced into these reservoirs. After separation of the first set of samples, the sample-reservoir body 13 is shifted to its original position as shown in FIG. 6a. At this position, samples in channels 18 may be injected into the separation channels 6 and separated. Separation channels are separating samples continuously and cathode reservoirs 3 serve as another set of sample reservoirs.

Injectors described in FIGS. 5 and 6 eliminated a delicate injection bar 12 of the three-piece fixed-volume-injectors as described in FIGS. 2, 3 and 5. Moving the sample-reservoir body 13 should be more robust than moving the injection bar 12. The accuracy of the injected volumes may not be as high and the injection volumes may not be as low as the three-piece fixed-volume-injectors.

In other preferred embodiments, reservoirs and channels are reconfigured as illustrated in FIG. 7 to overcome the problems of the two-piece fixed-volume-injectors. In this design, sample reservoirs 1 and anode reservoirs 4 are on the same piece while analyte waste reservoirs 2 and cathode reservoirs 3 are on the other. Also, channels 17 are connected to the separation channels 6 at positions 37 that are a finite distance away from the sliding interface. Channels 38 between point 37 and the sliding interface are the sample injectors. During sample loading, the cathode-reservoir body 35 is shifted to a loading position as illustrated in FIG. 7b. A sample loading voltage is applied between sample reservoirs 1 and analyte waste reservoirs 2. Samples are loaded in sample reservoirs 1, electrophoresed across channels 17 and 16 to the analyte waste reservoir 2. Then, cathode-reservoir body 35 is shifted back to its original position as shown in FIG. 7a. A separation voltage is applied between cathode reservoirs 3 and anode reservoirs 4 analytes in the injectors 38 are injected into the separation channels 6 and separated. Injector channels 38 may be made as short as tens of micrometers, preferably hundreds of micrometers, because they are microfabricated and then diced.

In additional embodiments, channels 17 are connected to the separation channels 6 through a short and narrow channel 42 (referring to FIG. 7c) or a pinhole 43 (referring to FIG. 7d) to prevent analytes from bleeding into the separation channels 6. Therefore, potentials applied to reservoirs do not need to be balanced. Referenced is made to copending U.S. patent application Ser. No. 10/076,042 entitled METHOD AND APPARATUS FOR SAMPLE INJECTION ON MICROFABRICATED DEVICES, concurrently filed on Feb. 11, 2002, which is assigned to MicroChem Solutions, Inc., the assignee of the present invention, and which had been fully incorporated by reference herein. The reference patent application describe in greater detail construction of the pinhole and narrow channel for sample injection.

In the injection schemes described in FIGS. 3, 5, 6 and 7, some of the reservoirs are moving with the chip piece to accomplish sample introduction and separation. In other preferred embodiments, referring to FIG. 8, all reservoirs are arranged on the separation-channel body 40 and only the injector channels 19 are located on the moving piece 39. While the moving piece 39 is in its original position as shown in FIG. 8a, samples are loaded in sample reservoirs 1 and a sample loading voltage is applied between sample reservoirs 1 and analyte waste reservoirs 2. Analytes are electrophoresed across channels 17, injector channels 19 and channels 16 to analyte waste reservoirs 2. Then, the moving piece 19 is shifted to sample injection and separation position as shown in FIG. 8b. As a separation voltage is applied between cathode reservoirs 3 and anode reservoirs 4, analytes in injector channels 19 are injected into the separation channels 6 for separation. Using this injection scheme, all reservoirs remain at fixed positions during operation.

Injector channels 19 are preferably have smaller dimensions than other channels. No balancing of the potentials applied to all reservoirs is required for all the injection schemes disclosed in this invention.

In a further embodiment, part or all of the reservoirs can be removed from the chip. Capillary tubes are used to connect part or all of the channels to appropriate containers outside the chip. Referenced is made to the copending U.S. patent application incorporated by reference above.

FIG. 9 illustrates an injector holder that may be designed to perform automated sample introduction and separation in accordance with one embodiment of the present invention. Referring to FIG. 9a and 9b, the holder 20 has a step 30 on the top. The flat region of the holder is slightly smaller than the chip that comprises a separation-channel body 11, an injection bar 12 and a sample-reservoir body 13. Heating or cooling elements may be included in this holder 20 to warm or cool the chip. The chip is put on the flat region of the holder with the sample-reservoir body 13 against the step 30. Two upside-down "L-shaped" clamps 21 are screwed down to a base (not shown) to secure the chip on the holder. The holder 20 and another strip 24 are also screwed down to the base to enable a spring 26 to bias a block 25 against the separation-channel body 11 of the chip. The strength of the spring 26 controls the tightness of the separation-channel body 11, injection bar 12 and sample-reservoir body 13 being held together. On each clamp 21 there is a step-hole 27, aligned with the injection bar 12 of the chip. A plunger 22 has a small head 23 with a cross-section slightly smaller than that of the injection bar 12. Plunger 22 is pneumatically operated in the step-hole 27. When the plunger is pressurized, it pushes towards the injection bar 12 but stops as the step-surface 33 of the plunger 22 contacts the step-surface 34 of the step-hole 27. When one plunger 22 on one side injection bar 22 is pushed in, the other plunger 22 on the other side of the injection bar 22 is pushed out, and vise versa. As the injection bar is moved back and forth, sample introduction and separation are carried out.

As illustrated in FIG. 9 and FIG. 10, separation channels 6 may be brought together forming a fan shape to facilitate scanning detection of multiple channels simultaneously, and all anode reservoirs are combined into a common reservoir to facilitate separation.

Schematic diagrams showing various embodiments of the fixed-volume-injectors of the present invention are provided in FIGS. 2 through 8. A variety of methods known in the art may be used to fabricate the fixed-volume-injectors. For example, the chip microfabrication protocols disclosed by S. Liu, et al., Analytical Chemistry 71 (1999) 566–573, or their equivalents known in the art can readily be adapted to produce the chip component of the present invention. Alternative methods known in the art may be employed within the scope of the present invention. For example, for photolithograpy, a thin sacrificial layer of Cr/Au (300 Å Cr and 0.5 $\mu$m Au) may be deposited onto a glass wafer, followed by a photoresist coating (Shipley photoresist 1818). After soft baking at 80° C., the photoresist may be exposed to UV radiation through a mask. The mask pattern will be transferred to the wafer after the photoresist is developed. After the exposed Cr/Au is etched off using gold and chromium etchants, the channel pattern is chemically etched into the glass. Concentrated HF may be used as the chemical etchant with an etching rate of ca. 7 $\mu$m per minute at 21° C. for borofloat glass. After etching, the residual photoresist and Cr/Au are stripped and access holes 33 if needed are drilled. The etched wafer may be thermally bonded with another wafer to enclose the grooves and form closed channels. The bonded chips are then taken to a dicing saw and diced to form the three-piece and two-piece fixed-volume-injectors.

While the embodiment in FIGS. 2, 4 and 9 are shown to comprise of separate pieces of separation-channel body 11, injection bar 12, and sample-reservoir body 13, it is noted that the separation-channel body 11 and the sample-reservoir body 13 may be configured in a single unitary body, with the sample injection bar 12 slidable between the separation-channel body 11 and the sample-reservoir body 13, without departing from the scope and spirit of the present invention.

The operations of the various embodiments of the present invention are controlled by a controller (not shown) to accomplish the functions recited herein. It would be within a person skilled in the art to implement the program code given the functions and features disclosed herein.

All of the methods and apparatus disclosed and claimed herein can be made and executed without undue experimentation in light of the present disclosure. While the invention has been described with respect to the described embodiments in accordance therewith, it will be apparent to those skilled in the art that various modifications and improvements may be made without departing from the scope and spirit of the invention. For example, it will be apparent to those of skill in the art that variations may be applied to the methods and apparatus and in the steps or in the sequence of steps of the methods described herein without departing from the concept, spirit and scope of the invention. It also will be apparent that certain substance such as polymeric and ceramic materials may be substituted for the glass materials described herein to achieve the same, similar or improved results. By way of example and not limitation, the sample injection concepts of the present invention is described in connection with capillary electrophoresis in a microfabricated chip. It is understood that the present invention is also applicable to bio-separation based on other than electrophoresis, and emissive radiation based detection such as fluorescence, phosphorescence, luminescence and chemi-luminescence as well as absorbance based detection. The sample introduction schemes of the present invention can be used for variety of applications, including integrated microfluidic systems for chemical analysis and sensing, and analytical separation techniques such as capillary electrophoresis, capillary electrochromatography, microcolumn liquid chromatography, flow injection analysis, and field-flow fractionation. A person skilled in the art will recognize that the instrument incorporating the essence of this invention can also be used for biomolecular analysis for DNA, proteins, carbohydrates, lipids, etc.

Furthermore, while the reaction channels in the described embodiments are defined by micro-separation channels etched in a substrate (micro-fluidics type devices or biochips), it is understood that the concepts of the present invention is equally applicable to columns or tubes defining the reaction channels.

All such similar substitutes and modifications apparent to those skilled in the art are deemed to be within the spirit, scope and concept of the invention as defined by the appended claims. Accordingly, it is to be understood that the invention is not to be limited by the specific illustrated embodiments, but only by the scope of the appended claims.

We claim:

1. A microfluidic device, comprising:
    a substrate comprising at least first and second blocks that are configured to slide relative to each another;
    at least one reaction channel defined on the first block along which the sample migrates;
    at least one sample channel defined on the first block;
    at least one sample metering channel defined on the second block;
    sliding means for sliding the second block relatively to the first block from a first position at which sample is loaded from the sample channel into the sample metering channel, to a second position at which sample is introduced from the sample metering channel to the reaction channel.

2. A microfluidic device as in claim 1, wherein the first block comprises a sample reservoir in a first section and a waste reservoir in a second section, wherein the second block slides between the first and second sections, with the sample metering channel in fluid communication with the sample reservoir and waste reservoir at the first position.

3. A microfluidic device as in claim 2, wherein the first block further comprises a first buffer reservoir in the first section and a second buffer reservoir in the second section, wherein at least one of the first and second buffer reservoirs is in fluid communication with the sample metering channel at the second position.

4. A microfluidic device as in claim 3, wherein the second block further comprises at least one auxiliary channel, wherein the auxiliary channel is aligned in fluid communication with at least one of the first and second buffer reservoir at the first position.

5. A microfluidic device as in claim 2, wherein the first and second sections of the first block are in separate pieces slidable relative to the second block.

6. A microfluidic device as in claim 5, wherein the first section of the first block moves with the second block when the second block slides from the first position to the second position.

7. A microfluidic device as in claim 6, wherein the first section of the first block slides relative to the second block to align the first and second buffer reservoir in fluid communication with the sample metering channel at the second position of the second block.

8. A microfluidic device as in claim 1, wherein the second block comprises at least one of a sample reservoir and waste reservoir in fluid communication with the sample metering channel, and the first block comprises at least one of a waste reservoir and sample reservoir complementary to said at least one of a sample reservoir and waste reservoir in the second block in fluid communication with the sample channel, wherein when the second block is at the first position, the sample reservoir, waste reservoir, sample channel and sample metering channel are aligned in fluid communication.

9. A microfluidic device as in claim 1, wherein the second block comprises first and second sample metering channels, wherein the second sample metering channel is positioned to permit sample loading from the sample channel to the second sample metering channel while sample is being introduced from the first sample metering channel to the reaction channel at the second position.

10. A microfluidic device as in claim 1, wherein the sample metering channel has two ends on a side of the second block that slides relative to the first block; and wherein the two ends of the sample metering channel are align in fluid communication with the sample channel at the first position, and with the reaction channel at the second position.

11. A microfluidic device as in claim 1, wherein there are a plurality of reaction channels, and wherein one end of the plurality of channels terminate at a same reservoir.

12. A microfluidic device as in claim 1, further comprising means for biasing the first and second blocks against each other in a slidable relationship.

13. A microfluidic device, comprising:

a substrate comprising at least first and second blocks that are configured to slide relative to each another;

at least one reaction channel defined on the first block along which the sample migrates;

at least one sample channel defined on the first block;

at least one sample metering channel defined on the first block;

at least one waste reservoir on the second block;

sliding means for sliding the second block relatively to the first block from a first position at which sample is loaded from the sample channel into the sample metering channel with excess discharged to the waste reservoir in the second block, to a second position at which sample is introduced from the sample metering channel to the reaction channel.

14. A method for injecting sample into a reaction channel defined on a microfluidic device, comprising the steps of:

providing a substrate comprising at least first and second blocks that are configured to slide relative to each another;

defining at least one reaction channel on the first block along which the sample migrates;

defining at least one sample channel on the first block;

defining at least one sample metering channel on the second block;

sliding the second block relatively to the first block from a first position at which sample is loaded from the sample channel into the sample metering channel, to a second position at which sample is introduced from the sample metering channel to the reaction channel.

* * * * *